(12) United States Patent
Bouvier et al.

(10) Patent No.: US 9,554,988 B2
(45) Date of Patent: Jan. 31, 2017

(54) METHOD FOR PREVENTING OR TREATING SKIN TUMOR

(75) Inventors: Guy Bouvier, Biot (FR); Matthew James Leoni, Hampton, NJ (US); Michael Graeber, Lawrenceville, NJ (US)

(73) Assignee: Galderma Research & Development, Biot (FR)

( * ) Notice: Subject to any disclaimer, the term of this patent is extended or adjusted under 35 U.S.C. 154(b) by 287 days.

(21) Appl. No.: 13/821,132

(22) PCT Filed: Jun. 29, 2011

(86) PCT No.: PCT/EP2011/060938
§ 371 (c)(1),
(2), (4) Date: Jun. 3, 2013

(87) PCT Pub. No.: WO2012/001064
PCT Pub. Date: Jan. 5, 2012

(65) Prior Publication Data
US 2013/0251649 A1    Sep. 26, 2013

Related U.S. Application Data

(60) Provisional application No. 61/344,334, filed on Jun. 30, 2010.

(51) Int. Cl.
| | | |
|---|---|---|
| *A61K 8/00* | (2006.01) | |
| *A61K 9/00* | (2006.01) | |
| *A61K 8/41* | (2006.01) | |
| *A61K 8/49* | (2006.01) | |
| *A61K 31/137* | (2006.01) | |
| *A61K 31/165* | (2006.01) | |
| *A61K 31/4174* | (2006.01) | |
| *A61Q 17/04* | (2006.01) | |
| *A61Q 19/04* | (2006.01) | |
| *A61K 31/402* | (2006.01) | |
| *A61K 9/12* | (2006.01) | |

(52) U.S. Cl.
CPC ............ *A61K 9/0014* (2013.01); *A61K 8/41* (2013.01); *A61K 8/4913* (2013.01); *A61K 8/4946* (2013.01); *A61K 8/4953* (2013.01); *A61K 31/137* (2013.01); *A61K 31/165* (2013.01); *A61K 31/402* (2013.01); *A61K 31/4174* (2013.01); *A61Q 17/04* (2013.01); *A61Q 19/04* (2013.01); *A61K 9/122* (2013.01)

(58) Field of Classification Search
None
See application file for complete search history.

(56) References Cited

U.S. PATENT DOCUMENTS

| | | |
|---|---|---|
| 5,935,962 A | 8/1999 | Thompson et al. |
| 2004/0170580 A1 | 9/2004 | Schmidt et al. |
| 2005/0020600 A1 | 1/2005 | Scherer |
| 2005/0059744 A1 | 3/2005 | Donello et al. |
| 2005/0276830 A1 | 12/2005 | DeJovin et al. |
| 2007/0082070 A1 | 4/2007 | Stookey et al. |
| 2007/0178138 A1 | 8/2007 | Pal et al. |
| 2011/0027247 A1* | 2/2011 | Narain ............... A61K 31/00 424/94.1 |
| 2011/0217249 A1* | 9/2011 | Dreher ............... A61K 9/0014 424/59 |
| 2011/0224216 A1 | 9/2011 | Andres et al. |

FOREIGN PATENT DOCUMENTS

| | | |
|---|---|---|
| RU | 2255765 C2 | 7/2005 |
| WO | 9107168 A1 | 5/1991 |
| WO | 0044404 A2 | 8/2000 |
| WO | 2011053487 A1 | 5/2011 |

OTHER PUBLICATIONS

Zhaboedov et al., "Adrenomimetics in the treatment of open-angle glaucoma," News of medicine and pharmacy, vol. 3. No. 8 (2010), available at http://www.mif-ua.com/archive/article_print/11649.
Office Action issued Sep. 23, 2015 in RU Application No. 2013125042 translation only.
Int'l Search Report issued Jan. 27, 2012 in Int'l Application No. PCT/EP2011/060938.
Scarparo et al, "Catecholamine effects on human melanoma cells evoked by alpha1-adrenoceptors," Archives of Dermatological research, vol. 296, No. 3, pp. 112-119 (Aug. 3, 2004).
Bruzzone et al, "alpha(2)-Adrenoceptor action on cell proliferation and mammary tumour growth in mice," British Journal of Pharmacology, vol. 155, No. 4, pp. 494-504 (Oct. 1, 2008).
Int'l Preliminary Report on Patentability issued Jan. 8, 2013 in Int'l Application No. PCT/EP2011/060938.
Int'l Search Report and Written Opinion issued Jan. 27, 2012 in Int'l Application No. PCT/EP2011/060939.
Kanno et al, "Stimulation of alpha2-adrenergic receptor inhibits cholangiocarcinoma growth through modulation of Raf-1 and B-Raf activities," Hepatology, vol. 35, No. 6, pp. 1329-1340 (Jun. 2002).
Int'l Preliminary Report on Patentability issued Jan. 8, 2013 in Int'l Application No. PCT/EP2011/060939.
U.S. Appl. No. 13/821,145 by Bouvier, filed Mar. 6, 2013.

* cited by examiner

*Primary Examiner* — Nannette Hollowman
(74) *Attorney, Agent, or Firm* — Panitch Schwarze Belisario & Nadel LLP (57) ABSTRACT

Methods, compositions and products for preventing skin tumor formation or inhibiting the development of an existing skin tumor in a subject are described. The methods involve administering to the subject a composition containing an α adrenergic receptor agonist, such as brimonidine.

15 Claims, 4 Drawing Sheets

Figure 1A. Prevalence by Week of First Perceptible Tumors Sexes combined

Figure 1B. Prevalence by Week of First 1 mm Tumors Sexes combined

Figure 1C. Prevalence by Week of First 2 mm Tumors Sexes combined

Figure 1D. Prevalence by Week of First 4mm Tumors Sexes combined

METHOD FOR PREVENTING OR TREATING SKIN TUMOR

CROSS-REFERENCE TO RELATED APPLICATION

This application is a Section 371 of International Application No. PCT/EP2011/060938, filed Jun. 29, 2011, which was published in the English language on Jan. 5, 2012, under International Publication No. WO 2012/001064 A1, and the disclosure of which is incorporated herein by reference.

BACKGROUND OF THE INVENTION

UV radiation has been shown to be a cause for a wide spectrum of skin damage, from premature aging to skin cancer, the most prevalent of all cancers in the United States. Skin cancer is a malignant neoplasm of the epidermis/dermis, i.e., it has uncontrolled growth, invades nearby tissue, and if left untreated, may spread throughout the body, metastasizing and eventually killing the host. Basal cell and squamous cell carcinomas represent the majority of skin cancer cases. The leading cause of death due to skin cancer is from malignant melanoma. It is estimated that over the lifetime 20% of United States population will develop skin cancer.

Besides skin cancer, there are also benign skin tumors and pre-malignant skin tumors. A benign skin tumor will not transform into skin cancer. Examples of benign skin tumors include, but are not limited to, moles, seborrheic keratoses, acrochordons (also called skin tags), epidermoid or sebaceous cysts, and dermatofibroma. A pre-malignant skin tumor is a confined mass that does not invade surrounding tissue, and is thus not yet cancerous by definition. However, over time they can dedifferentiate and become malignant. One common form of pre-malignant cancer is carcinoma in situ, where the cells are neoplastic and continue to multiply, but do not leave their confined space.

Skin tumors can be treated by various therapies, such as surgical removal or destruction via excision, cryosurgery, electro-cautery, chemo-cautery, and radiation or topical cytotoxic agents. If the malignant skin tumors are detected early, treatment is usually effective. However, the treatment can still be invasive.

An alpha adrenergic agonist is a drug that selectively stimulates alpha adrenergic receptors. The alpha-adrenergic receptor has two subclasses α1 and α2. Complete selectivity between receptor agonism is rarely achieved, some agents have partial selectivity.

The α adrenoceptor agonists have been used therapeutically for a number of conditions including hypertension, congestive heart failure, angina pectoris, spasticity, glaucoma, diarrhea, and for the suppression of opiate withdrawal symptoms (J. P. Heible and R. R. Ruffolo Therapeutic Applications of Agents Interacting with α-Adrenoceptors, p. 180-206 in *Progress in Basic and Clinical Pharmacology* Vol. 8, P. Lomax and E. S. Vesell Ed., Karger, 1991).

It was reported that activation of alpha-adrenoceptors with alpha-adrenoceptor agonists (e.g., clonidine, oxymetazoline, dexmedetomidine, etc) was associated with enhanced proliferation of human tumor epithelial breast cell lines or mouse mammary tumor cell line. See, e.g., Vazquez et al., *Cancer Chemother Pharmacol.* 2006 July; 58(1):50-61. Epub 2005 Nov. 15; and Bruzzone et al., *Br J Pharmacol.* 2008 October; 155(4):494-504. Epub 2008 Jul. 7. It was also reported that the alpha2-adrenoceptor antagonist yohimbine inhibited the proliferation and induced apoptosis of pancreatic cancer cells, suggesting that yohimbine can be used as an anticancer drug for pancreatic cancer. Shen et al., *World J. Gastroenterol.* 2008 Apr. 21; 14(15):2358-63. It was further reported that stimulation of alpha 2-adrenergic receptor inhibited cholangiocarcinoma, a cancer of the bile ducts. Kanno et al., *Hepatology,* 2002, Volume 35, Issue 6 (p 1329-1340). The current literature, while not extensive, does indicate that that alpha-adrenergic receptors may play a role in tumorogenesis, and that stimulation or antagonism of the these receptors can lead to either increased growth or suppression of tumor tissue, depending on the underlying cellular sub-type.

There is a need of improved noninvasive methods and compositions that would effectively prevent skin tumor formation or reduces skin tumor development, particularly for skin tumors induced by UV radiation. The present invention relates to such improved methods and compositions.

BRIEF SUMMARY OF THE INVENTION

It is now surprisingly discovered that treatment with an α adrenergic receptor agonist has resulted in a significant delay of skin tumor formation and a significant regression in skin tumor growth in subjects exposed to UV radiation.

In one general aspect, embodiments of the present invention relate to a method of preventing skin tumor formation in a subject. The method comprises administering to the subject a composition comprising an effective amount of an α adrenergic receptor agonist and a pharmaceutically acceptable carrier.

In another general aspect, embodiments of the present invention relate to a method of inhibiting the progression of an existing skin tumor in a subject, comprising administering to the subject a composition comprising a therapeutically effective amount of an α adrenergic receptor agonist and a pharmaceutically acceptable carrier.

In another general aspect, embodiments of the present invention relate to a method of inducing the death or inhibiting the growth of a skin tumor cell, comprising contacting the skin tumor cell with a composition comprising an α adrenergic receptor agonist in an amount sufficient to induce the death or inhibit the growth of the skin tumor cell, respectively.

In another general aspect, embodiments of the present invention relate to a method for protecting the skin, the lips, or the scalp of a subject against the damaging effects of UV-radiation. The method comprises administering to the subject a composition comprising a safe and effective amount of an α adrenergic receptor agonist.

In another general aspect, embodiments of the present invention relate to a method of tanning the skin of a subject, wherein the method comprises administering to the subject a composition comprising a safe and effective amount of an α adrenergic receptor agonist.

Another aspect of the present invention relates to a cosmetic product, comprising:

(1) a topical composition comprising a safe and effective amount of an α adrenergic receptor agonist; and (2) instructions on applying the topical composition to the skin, the lips, or the scalp of a subject against the damaging effects of UV-radiation.

Yet another aspect of the present invention relates to a topical composition for tanning the skin of a subject, comprising:

(1) a safe and effective amount of an α adrenergic receptor agonist and;

(2) a safe amount of a tanning agent.

Other aspects, features and advantages of the invention will be apparent from the following disclosure, including the detailed description of the invention and its preferred embodiments and the appended claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, an "α adrenergic receptor agonist" or "agonist of α adrenoceptor" means a compound that binds to and stimulates alpha adrenergic receptor subclass α.

As used herein, the name of a compound is intended to encompass all possible existing isomeric forms (e.g., optical isomer, enantiomer, diastereomer, racemate or racemic mixture), esters, prodrugs, metabolite forms, or pharmaceutically acceptable salts, of the compound.

The phrase "pharmaceutically acceptable salt(s)", as used herein, means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds used in the present invention can form pharmaceutically acceptable salts with various amino acids. Suitable base salts include, but are not limited to, aluminum, calcium, lithium, magnesium, potassium, sodium, zinc, and diethanolamine salts.

For a review on pharmaceutically acceptable salts see BERGE ET AL., 66 *J. PHARM. SCI.* 1-19 (1977), incorporated herein by reference.

As used herein, the term "hydrate" means a compound of interest, or a pharmaceutically acceptable salt thereof that further includes a stoichiometric or non-stoichiometric amount of water bound to it by non-covalent intermolecular forces.

In an embodiment of the present invention, the α adrenergic receptor agonists include, but are not limited, to the α1 adrenergic receptor agonists, such as oxymetazoline, tetrahydrozoline, nephazoline, xylometazoline and the α1-adrenoceptor agonists discussed in chapters 6 and 10 of Goodman and Gilman's The Pharmacological Basis of Therapeutics, Tenth Edition, edited by Hardman J and Limbird L. New York, N.Y., McGraw-Hill, 2001, which is hereby incorporated by reference as though set forth in full herein, and in particular phenylepherine methoxamine, mephentermine, metaraminol, desglymidodrine, and its prodrug midodrine.

The most preferred α1 adrenergic receptor agonists are phenylepherine and oxymetazoline and pharmaceutically acceptable salts thereof.

According to the present invention, α adrenergic receptor agonists can be administered to the subject through the routes of topical, epicutaneous, transdermal, subcutaneous, or intramuscular deliveries. In a preferred embodiment, α adrenergic receptor agonists are delivery to the site of the tumor or the skin area subject to UV damages by subcutaneous delivery or topical application on the skin.

As used herein, "topical application" and "topically applying" means directly laying on or spreading on the skin in need of treatment, e.g., by use of the hands or an applicator.

As used herein, "subcutaneous delivery" means directly depositing in or underneath the skin, or in the subcutaneous fat layer, by use of an applicator such as a needle, a multi-needle array, an energy-based delivery system capable of subcutaneous delivery, a pressure-based delivery system capable of subcutaneous delivery, a needleless delivery system capable of subcutaneous delivery, or a similar medical device.

As used herein, an "skin tumor" includes a skin cancer, a benign skin tumor and pre-malignant skin tumor. Skin cancers include, but are not limited to, basal cell and squamous cell carcinomas and malignant melanoma. Examples of benign skin tumors include, but are not limited to, moles, seborrheic keratoses, acrochordons (also called skin tags), epidermoid or sebaceous cysts, and dermatofibroma. Pre-malignant skin tumors include, but are not limited to carcinoma in situ.

One embodiment of the present invention relates to a method of preventing skin tumor formation in a subject, which comprises administering to the subject a composition comprising an effective amount of an α adrenergic receptor agonist and a pharmaceutically acceptable carrier.

As used herein, an "effective amount of an α adrenergic receptor agonist" means the amount of the α adrenergic receptor agonist that is sufficient to prevent or delay the formation of skin tumors in a tissue system, mammal or human.

As used herein, the term "subject" means any mammal, preferably a human, to whom will be or has been administered compounds or topical formulations according to embodiments of the invention.

As used herein, the term "composition" is intended to encompass a product comprising the specified ingredients in the specified amounts, as well as any product which results, directly or indirectly, from combinations of the specified ingredients in the specified amounts.

As used herein, "prevention" or "preventing" refers to a reduction of the risk of acquiring a skin tumor. In a preferred mode of the embodiment, the specified compounds are administered as a preventative measure to a subject having a predisposition to a skin tumor, even though symptoms of the disorder are absent or minimal.

As used herein, a "pharmaceutically-acceptable carrier" means a carrier that is suitable for the application of the present invention without undue toxicity, incompatibility, instability, irritation, allergic response, and the like. This term is not intended to limit the ingredient which it describes.

Another embodiment of the present invention relates to a method of inhibiting the progression of an existing skin tumor in a subject, which comprises administering to the subject a composition comprising a therapeutically effective amount of an α adrenergic receptor agonist and a pharmaceutically acceptable carrier.

As used herein, a "therapeutically effective amount of an α adrenergic receptor agonist" means the amount of the α adrenergic receptor agonist that is sufficient to prevent or delay the progression of skin tumors in a tissue system, mammal or human.

One skilled in the art will recognize that the therapeutically effective amount of the α adrenergic receptor agonist to be used in the instant invention can vary with factors, such as the particular subject, e.g., age, diet, health, etc., degree of UV radiation exposed to, severity and complications of the skin tumor sought to be treated or prevented, the formulation used, etc. In view of the present disclosure, standard procedures can be performed to evaluate the effect of the administration of a composition to a subject, thus allowing a skilled artisan to determine the therapeutically effective amount of the α adrenergic receptor agonist to be administered to the subject. For example, the clinically observable beneficial effect of the α adrenergic receptor agonist in preventing the formation or preventing or delaying the progression of a skin tumor.

The clinically observable beneficial effect can be a situation that, when a composition of the present invention is administered to a subject after signs and/or symptoms related to a skin tumor are observable, the signs and/or symptoms are prevented from further development or aggravation, or develop to a lesser degree than without administration of the specified composition according to embodiments of the present invention. The clinically observable beneficial effect can also be that, when a composition of the present invention is administered to a subject before signs and/or symptoms related to a skin tumor are observable, the signs and/or symptoms are prevented from occurring or subsequently occur to a lesser degree than without administration of the composition of the present invention.

In another embodiment, a therapeutically effective amount of the α adrenergic receptor agonist will reduce of the discomfort of the subject associated with the skin tumor or a sign and/or symptom associated therewith.

Methods of the present invention can be used in conjunction with one or more other treatments or medications for preventing the formation of a skin tumor or inhibiting the progression, or treating an existing skin tumor or a sign and/or symptom associated therewith.

For example, a therapeutically effective amount of an α adrenergic receptor agonist can be used in conjunction with a therapy for treating a skin tumor, such as surgery-scalpel, cryosurgery, electro-surgery, chemo-surgery, or radiation and cytotoxic agents, such as alkylating agents, e.g., nitrogen mustard, ethyleneimine, fluorouracil, icyclophosphamide; anti-metabolites, e.g., 8-azaguinine, 6-mercaptopurine, aminopterin, methotrexate; antibiotics, e.g., sarcomycin, adinomycin, carcinophyrin, mitomycin-C, chromomycin, bleomycin, vinblastine; hormones, e.g., sex hormones, ACTH, corticosteroids; radio-isotopes—P 32, I 131, Co 60, Au 190; or plant derivatives, e.g., podophyllin, colchicin, milkweed, or Abrus precatorius.

The other medicament or treatment can be administered to the subject simultaneously with, or in a sequence and within a time interval of, the administration of the α adrenergic receptor agonist, such that the active ingredients or agents can act together to treat or prevent skin tumor and signs and/or symptoms associated therewith. For example, the other medicament or treatment and the α adrenergic receptor agonist can be administered in the same or separate formulations at the same or different times.

Any suitable route of administration can be employed to deliver the additional treatment or medication including, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation.

Another embodiment of the present invention relates to a method of inducing the death or inhibiting the growth of a skin tumor cell, which comprises contacting the skin tumor cell with a composition comprising an α adrenergic receptor agonist in an amount sufficient to induce the death or inhibit the growth of the skin tumor cell, respectively. The cell under the treatment can be in a cell culture in vitro, or a cell within an mammal in vivo.

The present invention also relates to a method for protecting the skin, the lips or the scalp of a subject against the damaging effects of UV-radiation, wherein the method comprises administering to the subject a composition comprising a safe and effective amount of an α adrenergic receptor agonist.

As used herein, safe and effective amount of an α adrenergic receptor agonist refers to an amount of an α adrenergic receptor agonist sufficient to protect the skin against the damaging effects of UV-radiation, specifically the UV-induced skin tumors, but low enough to avoid serious side effects. The safe and effective amount of α adrenergic receptor agonist will vary with the age, health and environmental UV exposure of the subject, the duration and nature of the treatment, the specific ingredient, or composition employed, the particular pharmaceutically-acceptable carrier utilized, and like factors.

The α adrenergic receptor agonist can be administered together with a safe and effective amount of a sun screening agent, an agent that absorbs or reflects some of the UV radiation in sunlight to thus help protect the skin against sun or UV damages.

As used herein, "safe and effective" refers to an amount of a sun screening agent sufficient to provide photo protection when the composition is applied but not so much as to cause any unacceptable side effects or skin reactions. The amount varies depending upon the sun screening agent chosen and the desired Sun Protection Factor (SPF). Commercially available sunscreen products have SPF values ranging from 2 to 40 or more. According to embodiments of the present invention, a topical composition comprises a safe and UV-damage protectively effective amount of an α2 adrenergic receptor agonist, and about 1% to about 20%, by weight, of a sun screening agent.

The suitable sun screening agent is capable of being commingled with the α adrenergic receptor agonist used in the present invention in a manner such that there is no interaction which would substantially reduce the efficacy of the composition for skin tumor prevention and/or treatment and photoprotection. Numerous sun screening agents are suitable for use in combination with α2 adrenergic receptor agonist, including, but not limited to: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); Dihydroxycinnamic acid derivatives (umbelliferone, methylumbelliferone, methylaceto-umbelliferone); Trihydroxy-Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl)ether; Hydroquinone; Benzophenones (Oxybenzene, Sulisobenzone, Dioxybenzone, Benzoesorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-di-benzoylmethane. See, e.g., Segarin, et al., at Chapter VIII, pages 189 et seq., of *Cosmetics Science and Technology*.

Preferred sun screening agents useful in the compositions of the present invention include, e.g., 2-ethylhexyl p-methoxycinnamate, butyl methoxydibenzoylmethane, 2-hydroxy-4-methoxybenzophenone, octyl dimethyl p-aminobenzoic acid and mixtures thereof.

Another aspect of the present invention relates to a composition and a method of tanning the skin of a subject, wherein the method comprises administering to the subject the composition comprising a safe and effective amount of an α adrenergic receptor agonist.

As used herein, safe and effective amount of an α adrenergic receptor agonist refers to an amount of an α adrenergic receptor agonist sufficient to protect the skin against the damaging effects of UV-radiation, specifically the UV-induced skin tumors, but low enough to avoid serious side effects. The safe and effective amount of α adrenergic receptor agonist will vary with the tanning agent and the concentration thereof used with herein, the duration and nature of UV exposure by the subject, the duration and nature of the treatment, the specific ingredient, or composition employed, the particular pharmaceutically-acceptable carrier utilized, and like factors.

The α adrenergic receptor agonist can be administered together with a safe amount of a tanning agent, an agent that helps to increase and/or prolong skin tanning after exposure to natural or artificial sunlight. According to an embodiment of the present invention, a topical composition for tanning the skin of a subject comprises a safe and effective amount of an α adrenergic receptor agonist and a safe amount of a tanning agent.

The suitable tanning agent is capable of being commingled with the α adrenergic receptor agonist used in the present invention in a manner such that there is no interaction which would substantially reduce the efficacy of the composition for skin tumor prevention and/or treatment and skin tanning. Examples of the tanning agent that can be used in the present invention include, but are not limited to, tyrosine, riboflavin, collagen hydrolysate, and combinations thereof.

A composition according to embodiments of the present invention comprises an effective amount, or a therapeutically effective amount, or a safe and effective amount of an α adrenergic receptor agonist and a pharmaceutically acceptable carrier.

In view of the present disclosure, the composition can be formulated for various delivery routes, such as topical, epicutaneous, transdermal, subcutaneous, or intramuscular deliveries. In a preferred embodiment, the α adrenergic receptor agonists is formulated as a subcutaneous or topical formulation.

One embodiment of the present invention relates to a topical composition comprising a pharmaceutically acceptable carrier and a therapeutically effective amount of an α adrenergic receptor agonist. The carriers useful for topical delivery of the specified compounds according to embodiments of the invention can be any carrier known in the art for topically administering pharmaceuticals, including, but not limited to, pharmaceutically acceptable solvents, such as a polyalcohol or water; emulsions (either oil-in-water or water-in-oil emulsions), such as creams or lotions; micro emulsions; gels; ointments; liposomes; powders; and aqueous solutions or suspensions. The pharmaceutically acceptable carrier includes necessary and inert pharmaceutical excipients, including, but not limited to, binders, suspending agents, lubricants, flavorants, preservatives, dyes, and coatings.

The topical composition according to embodiments of the present invention are prepared by mixing a pharmaceutically acceptable carrier with a therapeutically effective amount of an α adrenergic receptor agonist according to known methods in the art, for example, methods provided by standard reference texts such as, REMINGTON: THE SCIENCE AND PRACTICE OF PHARMACY 1577-1591, 1672-1673, 866-885 (Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

In one embodiment, the topical composition of the invention is in the form of an emulsion. Emulsions, such as creams and lotions are suitable topical formulations for use in the invention. An emulsion is a dispersed system comprising at least two immiscible phases, one phase dispersed in the other as droplets ranging in diameter from 0.1 μm to 100 μm. An emulsifying agent is typically included to improve stability. When water is the dispersed phase and an oil is the dispersion medium, the emulsion is termed a water-in-oil emulsion. When an oil is dispersed as droplets throughout the aqueous phase as droplets, the emulsion is termed an oil-in-water emulsion. Emulsions, such as creams and lotions that can be used as topical carriers and their preparation are disclosed in REMINGTON: THE SCIENCE AND PRACTICE OF PHARMACY 282-291 (Alfonso R. Gennaro ed. 19th ed. 1995), hereby incorporated herein by reference.

In another embodiment, the topical composition of the invention is in the form of a gel, for example, a two-phase gel or a single-phase gel. Gels are semisolid systems consisting of suspensions of small inorganic particles or large organic molecules interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the invention are disclosed in REMINGTON: THE SCIENCE AND PRACTICE OF PHARMACY 1517-1518 (Alfonso R. Gennaro ed. 19th ed. 1995), hereby incorporated herein by reference. Other suitable gels for use with the invention are disclosed in U.S. Pat. No. 6,387,383 (issued May 14, 2002); U.S. Pat. No. 6,517,847 (issued Feb. 11, 2003); and U.S. Pat. No. 6,468,989 (issued Oct. 22, 2002), each of which patents is hereby incorporated herein by reference.

In an embodiment, the topical composition further comprises an aqueous gel comprising water and a water-gelling amount of a pharmaceutically acceptable gelling agent selected from the group consisting of carbomers, glycerine polyacrylate, and mixtures thereof, and the topical composition has a physiologically acceptable pH.

As used herein, "carbomer" is the USP designation for various polymeric acids that are dispersible but insoluble in water. When the acid dispersion is neutralized with a base a clear, stable gel is formed. Carbomer 934P is physiologically inert and is not a primary irritant or sensitizer. Other carbomers include 910, 940, 941, and 1342. Polymer thickeners (gelling agents) that may be used in compositions according to embodiments of the present invention include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B. F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Preferably the gelling agent comprises between about 0.2% to about 4% by weight of the composition. More particularly, the preferred compositional weight percent range for "CARBOPOL®" is between about 0.5% to about 2%, while the preferred weight percent range for "NATROLSOL®" and "KLUCEL®" is between about 0.5% to about 4%. The preferred compositional weight percent range for both "HYPAN®" and "STABILEZE®" is between 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

In another preferred embodiment, the topical composition of the invention is in the form of an ointment. Ointments are oleaginous semisolids that contain little if any water. Preferably, the ointment is hydrocarbon based, such as a wax, petrolatum, or gelled mineral oil. Suitable ointments for use in the invention are well known in the art and are disclosed in REMINGTON: THE SCIENCE AND PRACTICE OF PHARMACY 1585-1591 (Alfonso R. Gennaro ed. 19th ed. 1995), hereby incorporated herein by reference.

In an embodiment of the present invention, the topical composition of the invention comprises at least one of a cream and an ointment, each comprising an agent selected from the group consisting of stearic acid, stearyl alcohol, cetyl alcohol, glycerin, water, and mixtures thereof, and the topical composition has a physiologically acceptable pH.

In another embodiment, the topical composition of the invention is in the form of an aqueous solution or suspension, preferably, an aqueous solution. Suitable aqueous topical formulations for use in the invention include those disclosed in REMINGTON: THE SCIENCE AND PRACTICE OF PHARMACY 1563-1576 (Alfonso R. Gennaro ed. 19th ed. 1995), hereby incorporated herein by reference. Other suitable aqueous topical carrier systems include those disclosed in U.S. Pat. No. 5,424,078 (issued Jun. 13, 1995); U.S. Pat. No. 5,736,165 (issued Apr. 7, 1998); U.S. Pat. No. 6,194,415 (issued Feb. 27, 2001); U.S. Pat. No. 6,248,741 (issued Jun. 19, 2001); U.S. Pat. No. 6,465,464 (issued Oct. 15, 2002), all of which patents are hereby incorporated herein by reference.

The pH of the topical formulations of the invention are preferably within a physiologically acceptable pH, e.g., within the range of about 5 to about 8, more preferably, of about 5.5 to about 6.5. To stabilize the pH, preferably, an effective amount of a buffer is included. In one embodiment, the buffering agent is present in the aqueous topical formulation in an amount of from about 0.05 to about 1 weight percent of the formulation. Acids or bases can be used to adjust the pH as needed.

Tonicity-adjusting agents can be included in the aqueous topical formulations of the invention. Examples of suitable tonicity-adjusting agents include, but are not limited to, sodium chloride, potassium chloride, mannitol, dextrose, glycerin, and propylene glycol. The amount of the tonicity agent can vary widely depending on the formulation's desired properties. In one embodiment, the tonicity-adjusting agent is present in the aqueous topical formulation in an amount of from about 0.5 to about 0.9 weight percent of the formulation.

Preferably, the aqueous topical formulations of the invention have a viscosity in the range of from about 15 cps to about 25 cps. The viscosity of aqueous solutions of the invention can be adjusted by adding viscosity adjusting agents, for example, but not limited to, polyvinyl alcohol, povidone, hydroxypropyl methyl cellulose, poloxamers, carboxymethyl cellulose, or hydroxyethyl cellulose.

In a preferred embodiment, the aqueous topical formulation of the invention is isotonic saline comprising a preservative, such as benzalkonium chloride or chlorine dioxide, a viscosity-adjusting agent, such as polyvinyl alcohol, and a buffer system such as sodium citrate and citric acid.

The topical composition according to embodiments of the invention can comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), hereby incorporated herein by reference, including, but not limited to, protectives, adsorbents, demulcents, emollients, preservatives, antioxidants, moisturizers, buffering agents, solubilizing agents, skin-penetration agents, and surfactants.

In an embodiment, the topical composition of the invention further comprises one or more agent selected from the group consisting of a preservative, a local anesthetic and a skin humectant.

Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

The topical composition according to embodiments of the invention can include pharmaceuticals or their pharmaceutically acceptable salts, such as an α adrenergic receptor agonist, and optionally one or more other pharmaceutically active ingredients, including, but not limited to, corticosteroids and other anti-inflammatory agents, such as betamethasone, diflorasone, amcinonide, fluocinolone, mometasone, hydrocortisone, prednisone, and triamcinolone; local anesthetics and analgesics, such as camphor, menthol, lidocaine, and dibucaine, and pramoxine; antifungals, such as ciclopirox, chloroxylenol, triacetin, sulconazole, nystatin, undecylenic acid, tolnaftate, miconizole, clotrimazole, oxiconazole, griseofulvin, econazole, ketoconozole, and amphotericin B; antibiotics and anti-infectives, such as mupirocin, erythromycin, clindamycin, gentamicin, polymyxin, bacitracin, and silver sulfadiazine; and antiseptics, such as iodine, povidine-iodine, benzalkonium chloride, benzoic acid, chlorhexidine, nitrofurazine, benzoyl peroxide, hydrogen peroxide, hexachlorophene, phenol, resorcinol, and cetylpyridinium chloride.

In a preferred embodiment, a topical composition according to embodiments of the invention further comprises titanium dioxide ($TiO_2$), preferably at an amount that is sufficient to mask the color of brimonidine or another colored ingredient in the formulation, but would not cause irritation to the skin. $TiO_2$ may cause mild irritation and reddening to the eyes, thus eye contact with the $TiO_2$—containing topically administrable composition should be avoided.

Dosages and dosing frequency will be determined by a trained medical professional depending on the activity of the compounds used, the characteristics of the particular topical formulation, and the identity and severity of the dermatologic disorder treated or prevented.

In an embodiment of the present invention, the topical composition comprises 0.01% to 5% by weight of the α adrenergic receptor agonist. For example, the composition can comprise, 0.01%, 0.05%, 0.1%, 0.2%, 0.3%, 0.4%, 0.5%, 0.6%, 0.7%, 0.8%, 0.9%, 1%, 2%, 3%, 4% or 5%, by weight, of the α adrenergic receptor agonist.

To treat or prevent a skin tumor in view of the present disclosure, for example, the topical compositions of the invention are topically applied directly to the area exposed to sunlight or the otherwise affected area in any conventional manner well known in the art, e.g., by dropper or applicator stick, as a mist via an aerosol applicator, via an intradermal or transdermal patch, or by simply spreading a formulation of the invention onto the affected area with fingers. Generally the amount of a topical formulation of the invention applied to the affected skin area ranges from about 0.1 g/cm² of skin surface area to about 5 g/cm², preferably, 0.2 g/cm² to about 0.5 g/cm² of skin surface area. Typically, one to four applications per day are recommended during the term of treatment.

Another embodiment of the present invention relates to a cosmetic product, comprising:

(1) a topical composition comprising a safe and effective amount of an α adrenergic receptor agonist; and (2) instructions on applying the topical composition to the skin, the lips, or the scalp of a subject against the damaging effects of UV-radiation.

As used herein, the term "instructions" when used in the context of a kit includes a publication, a recording, a diagram or any other medium of expression which can be used to communicate the usefulness of the kit for its designated use. The instructions can, for example, be affixed to or included within a container for the kit.

The cosmetic product can further comprise a second topical composition comprising a safe and effective amount of a sun screening agent.

The α adrenergic receptor agonist and the sun screening agent can be formulated in the same or separate topical compositions contained in one or two separate containers, such as a dropper, a jar, or a tube with a suitable small orifice size, such as an extended tip tube, made of any pharmaceutically suitable material.

The topical formulations of the invention can be filled and packaged into a plastic squeeze bottle or tube. Suitable container-closure systems for packaging a topical formulations of the invention are commercially available for example, from Wheaton Plastic Products, 1101 Wheaton Avenue, Millville, N.J. 08332.

Preferably, instructions are packaged with the formulations of the invention, for example, a pamphlet or package label. The labeling instructions explain how to administer topical formulations of the invention, in an amount and for a period of time sufficient to treat or prevent a skin tumor and signs and/or symptoms associated therewith. Preferably, the label includes the dosage and administration instructions, the topical formulation's composition, the clinical pharmacology, drug resistance, pharmacokinetics, absorption, bioavailability, and contraindications.

This invention will be better understood by reference to the non-limiting examples that follow, but those skilled in the art will readily appreciate that the examples are only illustrative of the invention as described more fully in the claims which follow thereafter.

EXAMPLE 1

Aqueous Topical Formulations

This example illustrates aqueous topical formulations that can be used in the present invention.

A first aqueous solution topical formulation comprises: brimonidine tartrate (0.01% to 5% w/w); Puriteg (0.005% w/w) (stabilized chlorine dioxide) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

A second aqueous solution topical formulation comprises brimonidine tartrate (0.2% to 2% w/w); benzalkonium chloride (0.005% w/w.) as a preservative; and the inactive ingredients: boric acid; calcium chloride; magnesium chloride; potassium chloride; purified water; sodium borate;

sodium carboxymethylcellulose; sodium chloride; with hydrochloric acid and/or sodium hydroxide to adjust the pH to 5.6 to 6.6. The osmolality is in the range of 250-350 mOsmol/kg.

EXAMPLE 2

Cream or Ointment Topical Formulations

This example illustrates cream or ointment topical formulations that can be used in the present invention.

A first cream topical formulation (hydrophilic ointment) is described in Table 2 below.

TABLE 2

| Ingredient | Weight Percent |
|---|---|
| oxymetazoline | 0.01% to 5% |
| Stearic acid | 7% |
| Stearyl alcohol | 5% Cetyl alcohol |
| 2% Glycerin | 10% |
| Sodium lauryl sulfate | 1% |
| Propylparaben | 0.05% |
| Methylparaben | 0.25% |
| Disodium edetate | 0.055% |
| Distilled water | QS |
| TOTAL | 100% |

To make the formulation, the stearyl alcohol and the white petrolatum are melted on a steam bath, and warmed to about 75 degrees C. The other ingredients, previously dissolved in the water and warmed to 75 degrees C., are then added, and the mixture is stirred until it congeals. The mixture is then allowed to cool with stirring, and brimonidine tartrate is then added as a concentrated solution.

An ointment topical formulation (hydrophilic ointment) is described in Table 3 below.

TABLE 3

| Ingredients | Weight |
|---|---|
| phenylepherine | 20 g |
| Cholesterol | 30 g |
| Stearyl Alcohol | 30 g |
| White Wax | 80 g |
| White Petrolatum | 820-800 g |

To make the formulation, the stearyl alcohol and white wax are mixed together on a steam bath. The cholesterol is then added and stirred until it completely dissolved. The white petrolatum is then added and mixed. The mixture is removed from the bath, and stirred until it congeals. With continuous stiffing, brimonidine tartrate is added as a concentrated slurry.

EXAMPLE 3

Gel Topical Formulations

This example illustrates gel topical formulations that can be used in the present invention.

A first gel formulation is described in Table 4 below.

TABLE 4

| Ingredients | Weight % |
|---|---|
| Brimonidine tartrate | 0.01-5% |
| Methylparaben NF | 0.15% |
| Propylparaben NF | 0.03% |

TABLE 4-continued

| Ingredients | Weight % |
|---|---|
| Hydroxyethylcellulose NF | 1.25% |
| Disodium Edetate USP | 0.05% |
| Purified Water, USP | QS |
| TOTAL | 100% |

A second gel formulation is described in Table 5 below.

TABLE 5

| Ingredients | Weight % |
|---|---|
| Brimonidine tartrate | 0.5% |
| Methylparaben | 0.20% |
| Propylparaben | 0.05% |
| Carbomer 934P NF | 1.0% |
| Sodium Hydroxide | QS pH 7 |
| Purified Water, USP | QS |
| TOTAL | 100% |

The ingredients are mixed together and aqueous sodium hydroxide is slowly added to the mixture until a pH of about 7 is reached and the gel is formed.

A third gel formulation is described in Table 6 below.

TABLE 6

| Ingredient | Weight Percent |
|---|---|
| Brimonidine tartrate | 0.1-2% |
| Carbomer 934P | 1.25% |
| Methylparaben | 0.3% |
| Phenoxyethanol | 0.4% |
| Glycerin | 5.5% |
| 10% Titanium dioxide | 0.625% |
| Propylene glycol | 5.5% |
| 10% NaOH Solution | 6.5% |
| DI Water | QS |
| TOTAL | 100% |

A fourth gel formulation is described in Table 7 below.

TABLE 7

| Ingredients | Weight % |
|---|---|
| oxymetazoline | 0.01-5% |
| Methylparaben | 0.2% |
| Propylparaben | 0.05% |
| "CARBOPOL ®" | 1.0% |
| Triethanolamine | QS pH 7 |
| Water | QS |
| TOTAL | 100% |

The ingredients are mixed together and stirred. Triethanolamine is added until a pH of about 7 is attained.

EXAMPLE 4

Foam Topical Formulations

This example illustrates foam topical formulations that can be used in the present invention.

A first foam formulation is described in Table 8 below.

TABLE 8

| Ingredients | Amount (Weight %) |
| --- | --- |
| Brimonidine tartrate | 0.01-5 |
| Stearic Acid | 4.2 |
| Laureth-23 | 1.4 |
| Sodium Lauryl Sulfate | 0.5 |
| Triethanolamine | 2.2 |
| Butylated hydroxytoluene (BHT) | 0.01 |
| Fragrance | 0.5 |
| Aeron A-31 Propellant | 3 |
| Water | QS |
| TOTAL | 100 |

The water is heated to 80-85° C., after which stearic acid is added. Once the stearic acid is melted, the laureth-23 is added, melted, and mixed well. Next, triethanolamine is added and the resulting composition is mixed well for about 30 minutes to form a soap. The resulting soap is then cooled to about 65° C., after which sodium lauryl sulfate is added. The composition is then mixed well. Next, the BHT and the Brimonidine tartrate are added, followed by mixing. The resulting composition is then cooled to room temperature and the fragrance added. The product is packaged with the Aeron A-31 propellant in an aerosol can using conventional techniques and mechanically shaken for 5 minutes. The product dispenses as a cone-shaped spray that deposits onto the skin as a layer of rich lather that quickly covers a wide area of skin, and begins to relieve symptoms within about 2 minutes after application.

A second foam formulation is described in Table 9 below.

TABLE 9

| Ingredient | Amount (Weight %) |
| --- | --- |
| Brimonidine tartrate | 0.2-2 |
| Water | QS |
| Palmitic Acid | 2.12 |
| Laureth-23 | 0.93 |
| Triethanolamine (99%) | 1.13 |
| Cetyl Dimethicone Copolyol | 0.19 |
| Mineral Oil | 0.31 |
| Stearyl Alcohol | 0.31 |
| Lauramide DEA | 0.15 |
| PEG-150 Distearate | 0.05 |
| Imidazolidinyl Urea | 0.0016 |
| Methylparaben | 0.0005 |
| Propylparaben | 0.00003 |
| Freeze Dried Aloe Powder | 0.0015 |
| Fragrance | 0.50 |
| Aeron A-31 Propellant | 3.00 |
| TOTAL | 100 |

The aqueous phase is prepared as follows. The water is heated to 80° C., after which palmitic acid is added. Once the palmitic acid is melted, the laureth-23 is added, melted, and mixed well. Next, triethanolamine is added and the resulting composition is mixed well for about 15 minutes to form a soap.

Stearyl alcohol, mineral oil, lauramide DEA, cetyl dimethicone copolyol, PEG-1 50 distearate, and BHT are mixed and heated at 55° C. to form the oil phase. The oil phase is combined with the aqueous phase at 80° C. and mixed well for about 15 minutes. The resulting mixture is then cooled to room temperature and the imidazolidinyl urea, methylparaben, and propylparaben are added, and then mixed well. The brimonidine tartrate is then added, and mixed well. Next, the fragrance is added, followed by gentle mixing. The aloe is then dissolved in make-up water and added with slow mixing to form the product formulation which is then packaged in an aerosol can as described for the first foam formulation.

The product dispenses as a cone-shaped spray that deposits onto the skin as a layer of rich lather that quickly covers a wide area of skin, and begins to relieve symptoms within about 2 minutes after application.

A third non-soapy foam formulation is described in Table 10 below.

TABLE 10

| Ingredient | Amount (Weight %) |
| --- | --- |
| Brimonidine tartrate | 0.4-0.6 |
| Ethanol | 6 |
| Ethyl Ester of PVM/MA | 4 |
| Copolymer Dimethicone Copolyol | 0.1 |
| Water | QS |
| PVP/VA Copolymer | 1 |
| Sodium Lauryl Sulfate | 1 |
| Oleth-20 | 0.5 |
| Cocamide MEA | 0.05 |
| Methyl Paraben | 0.1 |
| Aminomethyl Propanol | 0.53 |
| Stearalkonium Chloride | 0.05 |
| Steareth-16 | 0.1 |
| Panthenol | 0.5 |
| Fragrance | 0.5 |
| Aeron A-46 | 5 |
| TOTAL | 100 |

The alcohol phase is prepared by dissolving ethyl ester of PVM/MA copolymer in ethanol, after which dimethicone is added and mixed well. The aqueous phase is prepared by heating the water to 65° C., after which the PVP/VA copolymer is added and mixed well. The oil phase is prepared by mixing the oleth-20, cocamide MEA, and steareth-16 at 60° C. to form a blend. The oil phase is then added to the aqueous phase at 65° C. and mixed well. Next, the methylparaben is added to the mixture, followed by mixing, after which the aminomethyl propanol, stearalkonium chloride, and panthenol are added and mixed until uniform. The resulting composition is cooled to room temperature, after which the alcohol phase is added and mixed well. The fragrance is then added and mixed gently to form the product. The product is then packaged in an aerosol can.

The product dispenses as a cone-shaped spray that deposits onto the skin as a layer of rich lather that quickly covers a wide area of skin, and begins to relieve symptoms within about 2 minutes after application.

EXAMPLE 5

Photo Carcinogenicity Study with Brimonidine

Albino hairless SKH1-hr mice (36/sex/group) were treated for 40 weeks with UVR and brimonidine gel or vehicle according to the design in table 11. Mice were further observed for 12 weeks without treatment. Topical treatments were performed approximately one hour before UVR on Monday, Wednesday and Friday of each week and approximately one hour after UVR Tuesday and Thursday of each week. See table 11.

All procedures involving animals were conducted in a fully accredited animal facility and in accordance with the preapproved protocols.

TABLE 11

| Dosage Group | Brimonidine tartrate Conc. (%) | Administration (μL/mouse, on 25 cm² BSA) | Frequency of administration (days per wk)* | Solar-simulated UVR dose (RBU/week) | Duration of Treatment or exposure (weeks) | Add'l Period w/o treatment or UVR exposure (weeks) |
|---|---|---|---|---|---|---|
| 1 | Vehicle | 100 | 5 | 600 | 40 | 12 |
| 2 | 0.18 | 100 | 5 | 600 | 40 | 12 |
| 3 | 1 | 100 | 5 | 600 | 40 | 12 |
| 4 | 2 | 100 | 5 | 600 | 40 | 12 |
| 5 | N/A | N/A | N/A | 600 | 40 | 12 |
| 6 | N/A | N/A | N/A | 1200 | 40 | 12 |

N/A: NOT APPLICABLE
RBU: Robertson-Berger Unit (a measure of effectiveness of UVR;
400 RBU approximates one minimal erythema dose in previously untanned human skin)
*Monday, Wednesday and Friday of each week: exposure to UVR approximately one hour after test item application.
Tuesday and Thursday of each week: exposure to UVR approximately one hour before test item application.

As the results shown in Table 12, topical application of Brimonidine at 0.18%, 1%, and 2% concentrations surprisingly slowed down development of skin tumor lesions. Brimonidine resulted in a dose-dependent delay in UV-induced skin tumor formation.

TABLE 12

Group Comparisons of Tumor Onset for Tumors ≥1 mm

| Parameter | Group 1 Vehicle + 600 RBU | Group 2 0.18% + 600 RBU | Group 3 1% + 600 RBU | Group 4 2% + 600 RBU | Group 5 (No treatment) 600 RBU | Group 6 (No treatment) 1200 RBU |
|---|---|---|---|---|---|---|
| Median Week(a) to Tumor (≥1 mm) | 40.5 | 48 | >52 | >52 | 40.5 | 26 |
| Tumor Yield(b) (≥1 mm) | 4.57 | 2.40 | 0.85 | 0.49 | 4.00 | 7.61 |

(a)The time at which one-half of the members of the groups have acquired one or more qualifying tumors.
(b)Average number of tumors per survivor The delay was observed in median week to tumor (≥1 mm) In fact, the 1% and 2% Brimonidine were so effective that less than one-half of the members of the groups acquired one or more qualifying tumors within the 52-week study period. The delay was also observed in tumor yield (≥1 mm) Compared to the vehicle group, 0.18% Brimonidine reduced the tumor yield by 1.7-fold, 1% Brimonidine by 4.7-fold; and 2% Brimonidine by 8.1-fold. These results represent a significant delay in onset tumor formation.

Figure 1A:
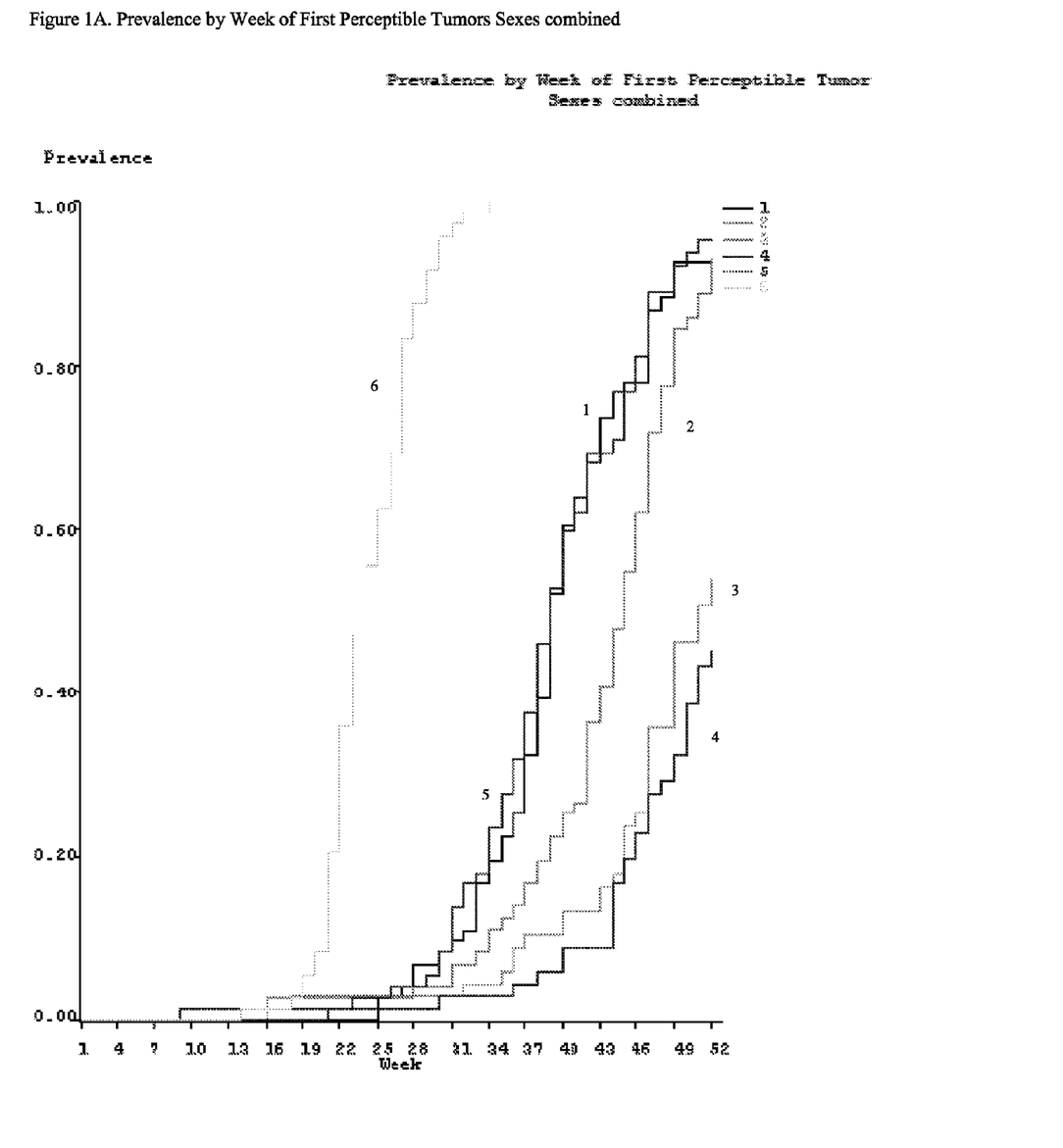
FIG. 1A. Prevalence by Week of First Perceptible Tumors Sexes combined.
Figure 1B:
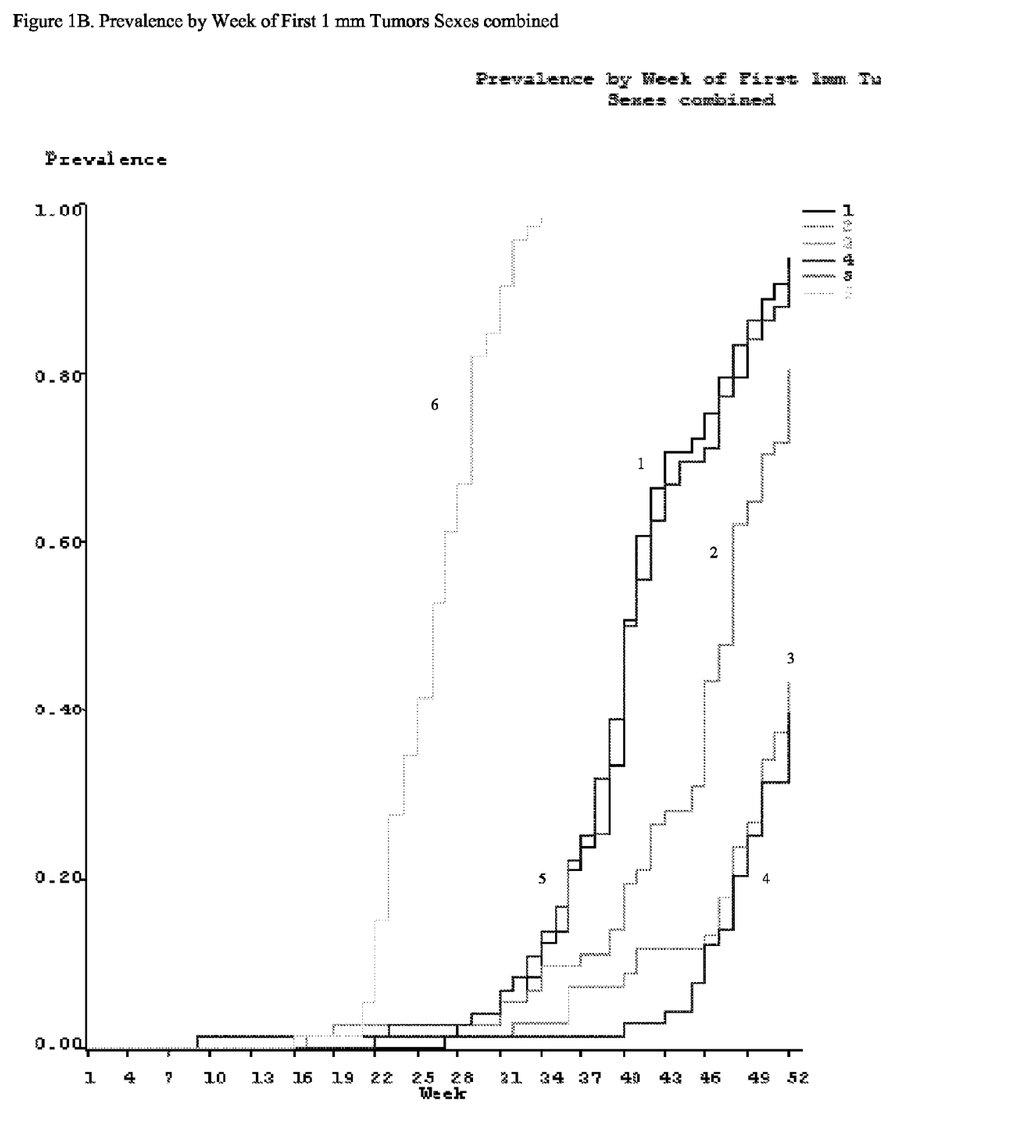
FIG. 1B. Prevalence by Week of First 1 mm Tumors Sexes combined.
Figure 1C:
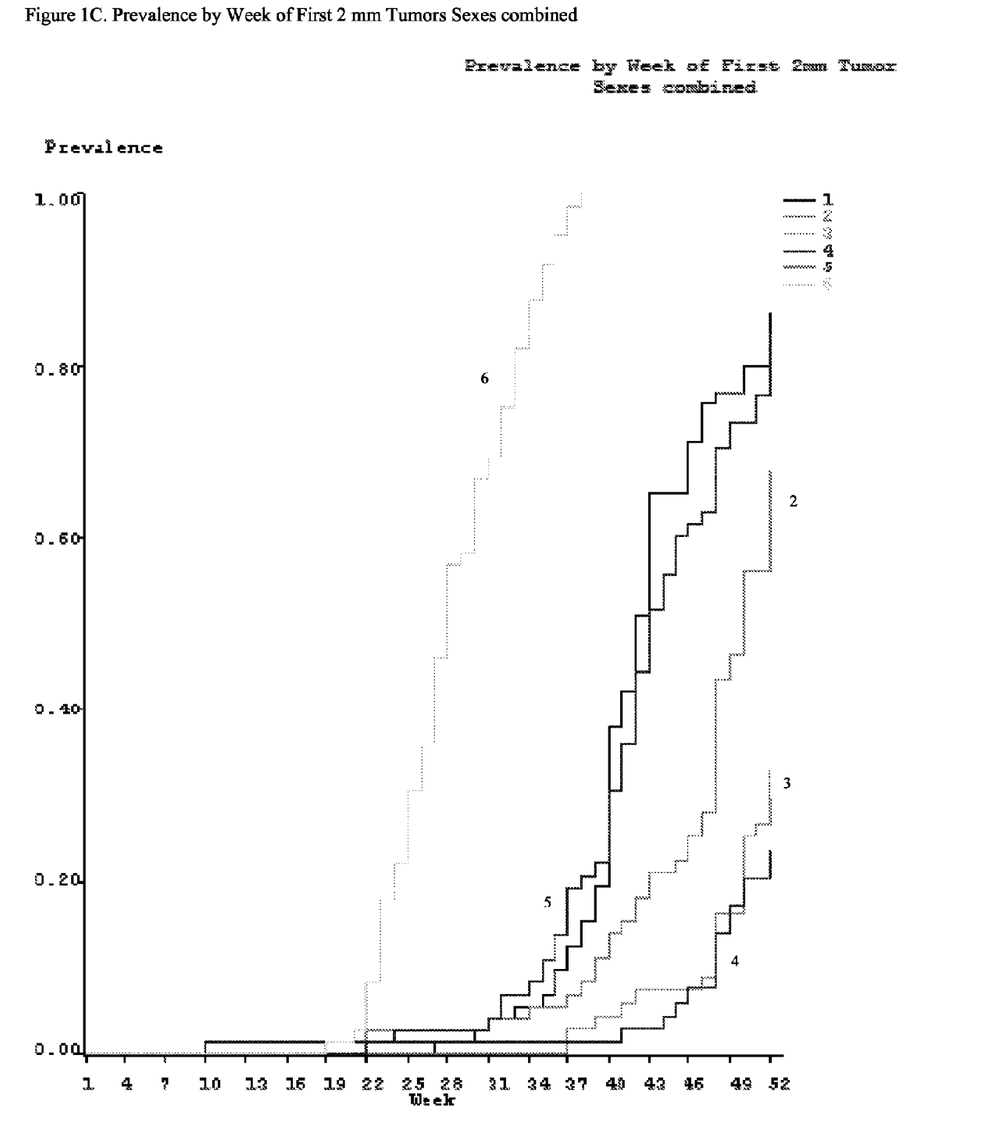
FIG. 1C. Prevalence by Week of First 2 mm Tumors Sexes combined.
Figure 1D:
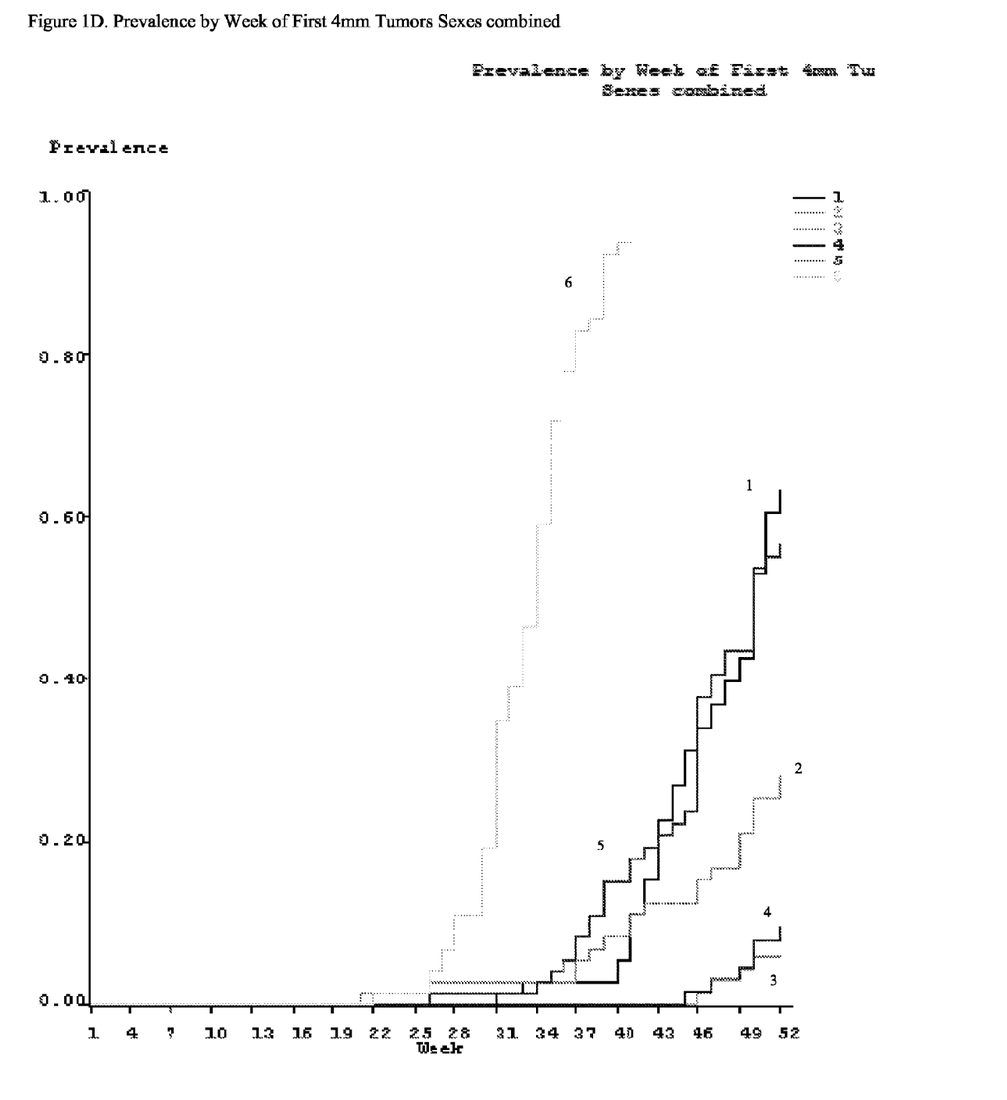
FIG. 1D. Prevalence by Week of First 4 mm Tumors Sexes combined.

Furthermore, FIG. 1 shows group comparisons of tumor prevalence. Note that the number next each line denotes the treatment group number shown in Tables 11 and 12. As shown in FIG. 1, with increasing Brimonidine concentration, the sizes of tumors were also reduced. This indicates that topical Brimonidine promote tumor regression as well.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of inducing the death or inhibiting the growth of a skin tumor cell, comprising contacting the skin tumor cell with a composition comprising an α1 adrenergic receptor agonist selected from the group consisting of mephentermine, metaraminol, desglymidodrine, and midodrine, in an amount sufficient to induce the death or inhibit the growth of the skin tumor cell, wherein the skin tumor cell is a cell of a skin cancer, a cell of a benign skin tumor selected from the group consisting of seborrheic keratoses, acrochordons, epidermoid, sebaceous cysts, and dermatofibroma, or a cell of a pre-malignant skin tumor.

2. The method according to claim 1, wherein the composition is delivered to a site of the skin tumor cell through a route of topical, epicutaneous, transdermal, subcutaneous, or intramuscular delivery.

3. The method according to claim 2, wherein the composition is delivered to the site of the skin tumor cell by subcutaneous delivery.

4. The method according to claim 2, wherein the composition is delivered to the site of the skin tumor cell by topical application.

5. The method according to claim 1, wherein the skin tumor cell is a cell of a skin cancer selected from the group consisting of basal cell carcinoma, squamous cell carcinoma, and malignant melanoma.

6. The method according to claim 1, wherein the skin tumor cell is a cell of a carcinoma in situ pre-malignant skin tumor.

7. The method according to claim 1, further comprising administering to the subject one or more other medicaments simultaneously with, or in a sequence and within a time interval of contacting the skin tumor cell with the composition.

8. The method according to claim 7, wherein the one or more other medicaments and the composition comprising are administered in the same formulation.

9. The method according to claim 1, wherein the α1 adrenergic receptor agonist is administered together with a safe and effective amount of a sun screening agent.

10. The method according to claim 1, wherein the α1 adrenergic receptor agonist is administered together with a safe and effective amount of a tanning agent.

11. The method according to claim 1, wherein the composition comprises 0.01% to 5% by weight of the α1 adrenergic receptor agonist.

12. The method according to claim 1, wherein the composition further comprises a pharmaceutically acceptable carrier.

13. The method according to claim 1, wherein the composition further comprises titanium dioxide.

14. The method according to claim 1, wherein the skin tumor cell is in a cell culture in vitro.

15. The method according to claim 1, wherein the skin tumor cell is within a mammal in vivo.

* * * * *